(12) United States Patent
Zanella et al.

(10) Patent No.: US 7,598,219 B2
(45) Date of Patent: Oct. 6, 2009

(54) IMPLANTS COMPRISING AN OSTEOINDUCTIVE FACTOR AND A CONTRAST AGENT COMPATIBLE THEREWITH

(75) Inventors: John M. Zanella, Cordova, TN (US); Steven Marquis Peckham, Memphis, TN (US)

(73) Assignee: Warsaw Orthopedic, Inc.

( * ) Notice: Subject to any disclaimer, the term of this patent is extended or adjusted under 35 U.S.C. 154(b) by 227 days.

(21) Appl. No.: 11/361,906

(22) Filed: Feb. 24, 2006

(65) Prior Publication Data

US 2007/0202048 A1    Aug. 30, 2007

(51) Int. Cl.
*A61K 38/16* (2006.01)
*A61K 38/17* (2006.01)
*A61K 38/18* (2006.01)

(52) U.S. Cl. .............................. 514/2; 514/12; 977/927; 977/928

(58) Field of Classification Search ........................ None
See application file for complete search history.

(56) References Cited

U.S. PATENT DOCUMENTS

| | | | |
|---|---|---|---|
| 6,033,438 A * | 3/2000 | Bianchi et al. ........... | 623/17.16 |
| 6,733,528 B2 * | 5/2004 | Abe et al. ................. | 623/11.11 |
| 2005/0119746 A1 | 6/2005 | Lidgren | |
| 2005/0142163 A1 * | 6/2005 | Hunter et al. ............... | 424/423 |
| 2005/0149175 A1 | 7/2005 | Hunter et al. | |
| 2005/0215874 A1 | 9/2005 | Wang et al. | |

OTHER PUBLICATIONS

"Oxilan", accessed Feb. 6, 2009 from http://www.guerbet-us.com/Oxilan_PI_2005.pdf.*

Zager et al., "Radiographic contrast media-induced tubular injury: evaluation of oxidant stress and plasma membrane integrity,"; Kidney Internationa, vol. 64 (2003), pp. 128-139.

Vitale et al., "Iodide excess induces apoptosis in thyroid cells through a p53-independent mechanism involving oxidative stress,"; Endocrinology (2000), vol. 141, No. 2, pp. 598-605.

Smiddy et al., "Transforming growth factor beta. A biologic chorioretinal glue,"; Archives of Opthalmology (Apr. 1989), vol. 107, No. 4, pp. 577-580.

* cited by examiner

*Primary Examiner*—Elizabeth C. Kemmerer

(57) ABSTRACT

The present invention is directed to methods, systems and reagents for providing contrast media that are compatible with osteoinductive factor induced bone formation.

9 Claims, No Drawings

IMPLANTS COMPRISING AN OSTEOINDUCTIVE FACTOR AND A CONTRAST AGENT COMPATIBLE THEREWITH

FIELD OF THE INVENTION

The present invention is directed to methods, systems and reagents for providing contrast media that are compatible with osteoinductive factor induced bone formation.

BACKGROUND OF THE INVENTION

Currently, biological agents are being used clinically to facilitate bone formation in bone grafting applications. Among the more common agents are demineralized bone matrix (DBM), bone marrow aspirate (BMA), and recombinant human bone morphogenetic proteins (BMP). Recombinant human Bone Morphogenetic Protein-2 (rhBMP-2) in combination with an Absorbable Collagen Sponge ("ACS"); (Integra LifeSciences Corporation, Plainsboro, N.J.) has been shown to induce bone formation in various clinical (Boden S. D., 24 *Orthop Nurs*, 49 (2005); Burkus J. K., et al, 15 *J Spinal Disorders*, 337 (2002); Govender S., et al, 84-A *J Bone Joint Surg.*, 2123 (2002); Khan S. N., et al, 4 *Expert Opin Biol Ther.*, 741 (2004); Haid R. W., et al, 4 *The Spine Journal*, 527 (2004); Sandhu H. S., et al, 28 *Spine*, S85 (2003); Termaat M. F., et al, 87 *Surg.*, 1367 (2005) and animal models (Akamaru T., et al: 28 *Spine*, 429(2003); Sandhu H. S., et al, 27 *Spine*, 567 (2002); Sandhu H. S., et al, 22 *Spine*, 1171 (1997)).

The rhBMP-2/ACS combination implant and the INFUSE® Bone Graft (Medtronic Sofamor Danek, Memphis, Tenn.), have been used as autograft replacement for lumbar spinal fusions, and subsequently approved for acute tibial fractures in 2004. (Termaat M. F., et al, 87 *Surg.*, 1367 (2005)). Autograft and many of the bone graft substitutes are radiopaque allowing surgeons to visualize the graft material placement using fluoroscopy or plain radiographs. INFUSE® Bone Graft is radiolucent and thus cannot be seen radiographically after implantation. (Burkus J. K., et al, 28 *Spine*, 372 (2003)). For surgeons used to working with metal implants, the sudden loss of verifying the implant placement on radiographs is a concern. There have been many inquiries into using radiopaque media in combination with INFUSE® Bone Graft. The concern however, with mixing these products is inactivating the rhBMP-2 that has been clinically shown to be equivalent to iliac crest autograft.

In view of the above considerations, it is clear that there is a need for an intraoperative radiographically visible product to supplement existing methods of implanting medical devices within a patient's body.

SUMMARY OF INVENTION

It has now been discovered that these and other long felt needs can be achieved by the present invention, which provides, in one aspect, methods, systems and reagents of providing contrast media that are compatible with osteoinductive factor induced bone formation.

Another aspect of the invention provides a method of intraoperative radiographic visualization of a location of a bone graft replacement in a patient comprising: (a) providing a composition to the patient comprising (1) a contrast media that is compatible with osteoinductive factor induced bone formation, (2) a osteoinductive factor, and (3) a bone graft matrix; and (b) radiographically visualizing a location of a bone graft replacement. In one embodiment of the invention the osteoinductive factor is selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, VEGF-A, VEGF-B, VEGF-C, VEGF-D VEGF-E, CTGF-1, CTGF-2, CTGF-3, osteoprotegerin, TGF-$\beta$-1, TGF-$\beta$-2, TGF-$\beta$-3, anti-TNF$\alpha$, PDGF-A, PDGF-B, PDGF-C, PDGF-D and GDF-5. In another embodiment the osteoinductive factor comprises a bone morphogenetic protein. In yet another embodiment the bone morphogenetic protein comprises a recombinant protein. In still another embodiment the recombinant bone morphogenetic protein comprises a human protein. Another embodiment of the invention provides that the recombinant human protein comprises BMP-2, BMP-4, BMP-7, or heterodimers thereof. In a preferred embodiment of the invention the recombinant human protein comprises BMP-2 and the bone graft matrix is an absorbable collagen sponge, more preferably the sponge is ACS.

Another aspect of the invention provides a method of treating or preventing a spinal disease or disorder, comprising a) surgically evacuating at least a portion of nucleus pulposus material and any free disc fragments from at least one intervertebral disc of a patient; b) preparing a composition comprising an interbody fusion device, contrast media, a bone graft matrix and a osteoinductive factor, wherein the contrast media is compatible with growth factor induced bone formation; and c) implanting the composition into the at least partially evacuated intervertebral disc space of the patient.

Another aspect of the invention provides a bone graft matrix composition comprising a contrast media, a bone graft matrix and a osteoinductive factor, wherein the osteoinductive factor is selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, VEGF-A, VEGF-B, VEGF-C, VEGF-D VEGF-E, CTGF-1, CTGF-2, CTGF-3, osteoprotegerin, TGF-$\beta$-1, TGF-$\beta$-2, TGF-$\beta$-3, anti-TNF$\alpha$, PDGF-A, PDGF-B, PDGF-C, PDGF-D and GDF-5.

These and other aspects of the present invention will be better appreciated by reference to the following detailed description. The detailed description and examples enhance the understanding of the invention, but are not intended to limit the scope of the invention.

DETAILED DESCRIPTION OF THE INVENTION

Degenerative disc disease occurs when discs in the spine are deteriorating or damaged, and can be extremely painful and debilitating in patients who generally lead active lives. Pain emanates from the damaged discs themselves or is caused by the discs or bone impinging on nearby nerve roots or the spinal cord. By the age of 50, approximately 85 percent of the population will show some evidence of disc degeneration. Spinal fusion, a commonly used surgical method of treating degenerative disc disease after conservative treatments have failed, essentially "welds" two vertebrae together to eliminate the pain caused by a damaged disc in the spine.

INFUSE® Bone Graft contains recombinant human bone morphogenetic protein (rhBMP-2), the genetically engineered version of a naturally occurring protein that is capable of initiating bone growth, or bone regeneration, in specific, targeted areas in the spine. It is a bone graft replacement currently approved by the FDA specifically for treating degenerative disc disease in the lumbar spine. The elimination of the hip graft harvesting procedure enables surgeons to avoid causing pain in one part of the body to cure it in another.

To use INFUSE® Bone Graft, surgeons reconstitute the rhBMP-2 powder with sterile water and then apply it to collagen sponges. The sponges are inserted inside medical devices, such as for example, LT-Cage, INTER FIX and/or INTER FIX RP Threaded Fusion Devices, a pair of which is then implanted between the vertebrae. Another aspect of the present invention, provides that the sponges are placed anterior or lateral to the implanted device. The thimble-like cages stabilize the spine while it is fusing and also maintain the proper height between the vertebrae. Until Applicants' invention surgeons were unable to visualize the rhBMP-2 sponge combination anterior or lateral to the device. The lack of verification of such implant placements on radiographs is a concern for surgeons.

The present invention fills a long felt need by providing methods, systems and reagents for visualization of the rhBMP-2 sponge combination inside the implant during surgical procedures. One aspect of the invention provides contrast media that are compatible with rhBMP-2 induced bone formation.

To aid in the understanding of the invention, the following non-limiting definitions are provided:

DEFINITIONS

The term "contrast media" refers to therapeutically and biologically inert diagnostic imaging agents that are injected into the body for use in organ or tissue enhancement in CT, X-Ray and Flouroscopy. Contrast media increase the contrast between a specific structure and the background, which improves conspicuity of the structure thereby enabling improved evaluation. To be effective, the contrast media must interfere with the wavelength of electromagnetic radiation used in the imaging technique, alter the physical properties of tissue to yield an altered signal, or, as in the case of radiopharmaceuticals, provide the source of radiation itself. Computed tomography (CT) is a valuable diagnostic imaging technique for studying various areas of the body. In CT, the radiodensity (electron density) of matter is measured and is expressed in terms of Hounsefield Units (HU). Hounsefield Units, named after the inventor of the first CT scanner, are an indication of the relative absorption of CT X-rays by matter, the absorption being directly proportional to the electron density of that matter. Water, for example, has a value of 0 HU, air a value of −1000 HU, and dense cortical bone a value of 1000 HU. Because of the similarity in the densities of various tissues in the body, however, it has been necessary to develop contrast agents which can be used to change the relative densities of different tissues. This has resulted in an overall improvement in the diagnostic efficacy of CT. In the search for contrast agents for CT, researchers have generally sought to develop agents that will increase electron density in certain areas of a region of the body (positive contrast agents). Barium and iodine compounds, for example, have been developed for this purpose. Magnetic resonance imaging (MRI) is another diagnostic imaging technique which may be used for producing cross-sectional images of the body in a variety of scanning planes such as, for example, axial, coronal, sagittal or orthogonal. MRI employs a magnetic field, radio frequency energy and magnetic field gradients to make images of the body. The contrast or signal intensity differences between tissues mainly reflect the T1 (longitudinal) and T2 (transverse) relaxation values and the proton density, which generally corresponds to the free water content, of the tissues. To change the signal intensity in a region of a patient by the use of a contrast medium, several possible approaches are available. For example, a contrast medium may be designed to change T1, T2, or the proton density. In the past attention has focused primarily on paramagnetic contrast agents for MRI. Paramagnetic contrast agents involve materials which contain unpaired electrons. The unpaired electrons act as small magnets within the main magnetic field to increase the rate of longitudinal (T1) and transverse (T2) relaxation. Paramagnetic contrast agents typically comprise metal ions, for example, transition metal ions, which provide a source of unpaired electrons. Nitroxides are another class of MRI contrast agent which are also paramagnetic. Complexes between gadolinium or other paramagnetic ions and organic ligands are widely used to enhance and improve MRI contrast. Gadolinium complexes increase contrast by increasing the nuclear magnetic relaxation rates of protons found in the water molecules that are accessible to the contrast agents during MRI (Caravan, P., et al., *R. B. Chem. Rev.* 99, 2293 (1999)). The relaxation rate of the protons in these water molecules increases relative to protons in other water molecules that are not accessible to the contrast agent. This change in relaxation rate leads to improved contrast of the images. In addition, this increase in relaxivity within a specific population of water molecule protons can result in an ability to collect more image data in a given amount of time. This in turn results in an improved signal to noise ratio. Imaging may also be performed using light, in which case an optical dye is chosen to provide signal. In particular, light in the 600-1300 nm (visible to near-infrared) range passes relatively easily through biological tissues and can be used for imaging purposes. The light that is transmitted through, or scattered by, reflected, or re-emitted (fluorescence), is detected and an image generated. Changes in the absorbance, reflectance, or fluorescence characteristics of a dye, including an increase or decrease in the number of absorbance peaks or a change in their wavelength maxima, may occur upon binding to a biological target, thus providing additional tissue contrast. In some situations, for example the diagnosis of disease close to the body surface, UV or visible light may also be used.

The term "bone graft matrix" refers to biomaterials for the orthopedic implant market which when placed in a bone defect provide scaffolding around which the patient's new bone will grow, gradually replacing the graft as the site heals. Examples of suitable bone graft matrices may include but are not limited to the Absorbable Collagen Sponge ("ACS") produced by Integra LifeSciences Corporation, Plainsboro, N. J.; and Collagraft® Bone Graft Matrix produced by Zimmer Holdings, Inc., Warsaw, Ind.; tricalcium phosphate granules e.g. ChronOS® or Ceros® TCP produced by Mathys Ltd., Switzerland; Norian injectable cements marketed by Norian/Synthes, USA; porous bone graft substitute e.g. ProOsteon Implant 500® marketed by Interpore Int., USA; micro glass granules e.g. BiGran® marketed by Orthovita, USA; calcium phosphate e.g. Alpha BSM®, marketed by ETEX Corp., USA; calcium phosphate-based bone cement e.g. BoneSource®, marketed by Orthofix Inc., USA; gel, putty and flex forms e.g. Grafton DMB®, marketed by Osteotech Inc., USA; artificial formable bone matrix marketed by Bioapatite AB, Sweden; bovine skin collagen fibers coated with hydroxyapatite e.g. Healos® marketed by Johnson & Johnson, USA; collagen sponges e.g. Hemostagene® marketed by Coletica SA, France, or e.g. Helisat® marketed by Integra Life Sciences Inc., USA; bioresorbable polymer and bone cement e.g. OrthoDyn marketed by DynaGen Inc., USA; biodegradable POB/PBT copolymers marketed by IsoTis B. V., Netherlands; biodegradable polymers e.g. Prolease® and Medisorb® marketed by Alkermes, USA.

The term "morphogen" refers to an osteoinductive factor that stimulates or induces bone growth. Examples of osteoinductive factors include, but are not limited to, Bone Morphogenetic Proteins (BMPs), including BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, and BMP-18; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Osteoprotegerin, Transforming Growth Factor betas (TGF-βs), including TGF-β-1, TGF-β-2, and TGF-β-3; inhibitors for tumor necrosis factor (e.g., anti-TNFα); and Platelet Derived Growth Factors (PDGFs), including PDGF-A, PDGF-B, PDGF-C, PDGF-D, and GDF-5. The polynucleotides encoding the same may also be administered as gene therapy agents. The preferred osteoinductive factors are the recombinant human bone morphogenetic proteins (rhBMPs) because they are available in unlimited supply and do not transmit infectious diseases. Most preferably, the bone morphogenetic protein is a rhBMP-2, rhBMP-4, rhBMP-7, or heterodimers thereof.

In some embodiments, the osteoinductive compositions used in this invention further comprise a therapeutically effective amount to stimulate or induce bone growth of a substantially pure bone inductive or growth factor or protein in a pharmaceutically acceptable carrier. The preferred osteoinductive factors are the recombinant human bone morphogenetic proteins (rhBMPs) because they are available in unlimited supply and do not transmit infectious diseases. Most preferably, the bone morphogenetic protein is a rhBMP-2, rhBMP-7 or heterodimers thereof. However, any bone morphogenetic protein is contemplated including bone morphogenetic proteins designated as BMP-1 through BMP-18. BMPs are available from Wyeth, Madison, N.J. and may also be prepared by one skilled in the art as described in U.S. Pat. No. 5,187,076 U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. Osteoinductive factors included within the scope of the present invention are BMP-1, BMP-2, rhBMP-2, BMP-3, BMP-4, rhBMP-4, BMP-5, BMP-6, rhBMP-6, BMP-7[OP-1], rhBMP-7, BMP-8, BMP-9, BMP-10, BMP-11, BMP-12, BMP-13, BMP-14, BMP-15, BMP-16, BMP-17, BMP-18, GDF-5, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II), and rhGDF-5. All osteoinductive factors are contemplated whether obtained as above or isolated from bone. Methods for isolating bone morphogenetic protein from bone are described in U.S. Pat. No. 4,294,753 to Urist and Urist et al., 81 PNAS 371, 1984.

The term "treating" or "treatment" of a disease refers to executing a protocol, which may include administering one or more compositions to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

The term "patient" refers to a biological system to which a treatment can be administered. A biological system can include, for example, an individual cell, a set of cells (e.g., a cell culture), an organ, a tissue, or a multi-cellular organism. A patient can refer to a human patient or a non-human patient.

By "comprising" is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The present invention provides methods, systems and reagents for providing contrast media that are compatible with osteoinductive factor induced bone formation. In this aspect of the invention the method provides intraoperative radiographic visualization of a location of a bone graft replacement in a patient comprising: (a) providing a composition to the patient comprising (1) a contrast media that is compatible with osteoinductive factor induced bone formation, (2) a osteoinductive factor, and (3) a bone graft matrix; and (b) radiographically visualizing of a location of a bone graft replacement in a patient.

The invention is based, in part, on the identification that INFUSE® Bone Graft combined with reconstituted rhBMP-2 in contrast media could be visualized radiographically. Applicants' invention permits for the first time the ability of the surgeon to visualize and evaluate the localization of the implant in the patient.

The osteoinductive compositions used in this invention comprise a therapeutically effective amount of the morphogen.

Bone morphogenetic proteins, such as rhBMP-2 work by causing primitive undifferentiated stem cells to become cartilage and bone-forming cells. It does this by causing undifferentiated stem cells to differentiate and evolve into mature bone-forming cells. Several hundred experimental studies have been published that have shown that rhBMP-2 is equal to and in most cases superior to utilizing the patient's own bone. Pre-clinical studies have shown that the new induced bone formation is faster and results in a higher fusion rate than utilizing the patient's own bone, harvested form the iliac crest. Histology or microscopic studies have proven that the formation of normal bone takes place, a process called "osteoinduction". rhBMP-2 appears to be extremely osteoinductive, and depending upon its proper use with a good carrier, drives the process of natural bone formation.

Recombinant BMP-2 can be used at a concentration of about 0.1 mg/ml to about 1.5 mg/ml, preferably near 1.5 mg/ml. However, any bone morphogenetic protein is contemplated including bone morphogenetic proteins designated as BMP-1 through BMP-18. BMPs are available from Wyeth, Madison, N.J. and the BMPs and genes encoding them may also be prepared by one skilled in the art as described in U.S. Pat. No. 6,858,431 to Hair et al.; U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat.

No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

Contrast media are intended to be therapeutically and biologically inert when injected into the body for use in organ or tissue visualization enhancement in CT, x-ray, and fluoroscopy imaging procedures. The first test performed in cadavers sought to determine whether INFUSE® Bone Graft combined with contrast media could be visualized radiographically and to determine the minimal percentage of dilution needed. The subsequent in vivo rat ectopic implant study used a validated animal model to determine the effect of using contrast media to reconstitute rhBMP-2 on the osteoinductivity of the morphogen when compared to control implants in which rhBMP-2 was reconstituted with sterile water for injection (WFI) in the standard fashion.

Radiographic visualization of implanted bone graft substitutes is a desirable feature for surgeons. INFUSE® Bone Graft, the first rhBMP product to gain FDA approval in spinal applications (FDA New Device Approval: InFUSE™ Bone Graft/LT-CAGE™ Lumbar Tapered Fusion Device—P000058 (2002); is radiolucent. Given the known sensitivity of osteoinductivity to rhBMP concentration, the addition of liquid contrast agents to the rhBMP-2 solution could result in loss of biologic activity. In fact, Applicants discovered that two of the three contrast agents evaluated in applicants system resulted in substantial inhibition of the bone forming activity of rhBMP-2.

The radiopaque compounds used clinically are primarily barium salt powders or contrast media. Most of these compounds rely on heavy metals to increase the radiographic image contrast of anatomical structures that are not normally easily visualized. These compounds are designed to be therapeutically and biologically inert when injected into the body for use in organ or tissue enhancement in CT, X-ray and fluoroscopy imaging procedures. Despite the intention, the heavy metals required for image enhancement may inactivate proteins with which the media interact, especially at high concentrations. (Semour S. B., *Disinfection, Sterilization, and Preservation*, Fourth edition (1991)). In the case of INFUSE® Bone Graft, inactivation of rhBMP-2 could result in a non-union across the implanted disc space and failure of a surgical procedure, some of which are highly invasive.

All of the contrast media used in the in vivo rat study contain a chelating agent. Conray® and Optiray® both contain EDTA calcium disodium, while the main component of Omniscan™, gadodiamide, is a small molecular weight, linear chelate. Chelates are molecular structures with negatively charged groups surrounding a metallic ion, and are used clinically to bind and remove heavy metals such as lead and mercury. The presence of a chelating agent would benefit rhBMP-2 protein function in the microenvironment created by the presence of the contrast media, although a chelating agent might inhibit mineralization of osteoid.

Another shared chemical property between Conray® and Optiray® is that their acting agent is iodinated. Iodine is also an oxidizing agent. Most proteins function in reducing environments, thus the iodine which is in the main component of these agents creates an environment that severely reduces the efficiency of rhBMP-2 or inhibits rhBMP-2 function. Another explanation for the results seen in the Conray® group that may extend to Optiray® is that the primary function of Conray® is to bind to plasma proteins. Conray® may bind to other proteins, like rhBMP-2, and this binding could inhibit protein function.

Applicants have shown that clear differences exist between the different contrast agents' effect on the osteoinductive function of rhBMP-2 in rats. It is suggested that radiopaque agents that utilize iodine should not be used in conjunction with rhBMP-2. Omniscan™ reconstituted rhBMP-2 induced bone formation was equivalent to the WFI saturated rhBMP-2 controls by semi-quantitative histology in the rat SC assay model. Both Conray™ and Optiray™ inhibited the osteoinductive potential of rhBMP-2.

The following examples are provided to assist in a further understanding of the invention. The particular materials and conditions employed are intended to be further illustrative of the invention and are not limiting upon the reasonable scope thereof.

EXAMPLES

Initial in vitro and cadaver tests verified the potential of using contrast media to visualize the INFUSE® Bone Graft implant on fluoroscopic radiographic images. Applicants evaluated the rehydration of the lyophilized rhBMP-2 powder with contrast media instead of the recommended sterile water. A reconstituted solution that consisted of 97% contrast media was applied to a 0.5 cc collagen sponge to produce a graft with a rhBMP-2 concentration of 0.1 mg/cc and implanted subcutaneously on the thoracic cavity of athymic rats. At four weeks, the rats were euthanized and the implants removed. The explants were graded by manual palpation, radiography, and histology.

By all methods evaluated, Omniscan™ was equivalent to the sterile water saturated rhBMP-2 controls; whereas Conray® and Optiray® were both shown to inhibit the osteoinductive potential of rhBMP-2.

Example 1

Fluoroscopy Lab

Following the instruction for use for the Large INFUSE® Bone Graft Kit, 8.4 ml of fluid contrast media (Conray®, Mallinckrodt Imaging Tyco Healthcare, Hazelwood, Mo.; and Oxilan® 300, Guerbert LLC, Bloomington, Ind.) was injected into a vial of lyophilized rhBMP-2 buffer (The rhBMP-2 buffer does not contain rhBMP-2 protein). Each ml of rhBMP-2 Buffer contains 5.0 mg sucrose, 25 mg glycine, 3.7 mg L-glutamic acid, 0.1 mg sodium chloride, and 0.1 mg polysorbate 80. After reconstituting the powder, 1.4 ml of each solution was applied to a 2.5 cm×5.0 cm×0.35 cm ACS, and fluoroscopic (Siemens Siremobile Iso-C Ser#389427, Muenchen, Germany) images of the flat, wetted sponge were obtained. The procedure was repeated with a 50:50 (v/v) mix of WFI/contrast media. Fluoroscopic images were also obtained of the rolled sponges.

Sol-O-Pake® (E-Z-EM, Inc., Westbury, N.Y.) powder, a barium sulfate salt, was sprinkled on an ACS wetted with WFI. Fluoroscopic images of ACS were obtained as the sponge lay flat, and again after it had been rolled-up.

Example 2

Cadaver Lab

Using the volumetric markings on a 5 cc syringe (Becton Dickinson & Co, Franklin Lakes, N.J.) and the dilution scheme presented in Table 1, 1.5 ml fluid was mixed in the syringe before being applied to the ACS. After waiting a minimum of 15 minutes, the ACS was rolled and placed in the interbody disc space of a human cadaver. The ACS was placed in a lumbar disc space with forceps and its position was verified by fluoroscopic imaging.

TABLE 1

Dilution Scheme

| Percentage (%) | Volume Oxilan 300 (ml) | Volume rhBMP-2 Buffer* (ml) |
|---|---|---|
| 100% | 1.4 | 0 |
| 57% | 0.8 | 0.6 |
| 29% | 0.4 | 1.0 |
| 14% | 0.2 | 1.2 |

*The rhBMP-2 Buffer does not contain rhBMP-2 protein. Each ml of rhBMP-2 Buffer contains 1.0 ml of sterile water, 5.0 mg sucrose, 25 mg glycine, 3.7 mg L-glutamic acid, 0.1 mg sodiun chloride, and 0.1 mg polysorbate 80.

Example 3

Rat Ectopic Model

Study Design:

This aspect of the invention was designed to evaluate the ability of rhBMP-2 to induce de novo bone in the presence of various contrast media in the rat ectopic model. 200 µL of a 0.1 mg/ml rhBMP-2 solution was applied to 0.5 cc collagen sponge discs (Kensey Nash, Exton, Pa.). After a 15-minute soak time, the rhBMP-2/collagen was implanted into a subcutaneous (SC) tissue pocket above the rib cage muscle of an athymic rat. There were four implants per rat. Contrast media represented 97% of the rhBMP-2 fluid suspension applied to the collagen disc. The rhBMP-2 buffer served as a control test fluid. The three commercially available contrast media used in this study were Conray®, Optiray® (Mallinckrodt Imaging Tyco Healthcare, Hazelwood, Mo.), and Omniscan™ (GE Healthcare, Princeton, N.J.). The study protocol was evaluated and approved by the Institutional Animal Care and Use Committee of the Atlanta Veterans Affairs Medical Center.

Material Preparation:

A 4.0 mg/ml rhBMP-2 solution was made by withdrawing 1.8 ml of sterile WFI and reconstituting a 7.2 mg vial of lyophilized rhBMP-2 protein powder to create a stock solution. This solution was diluted 1:34 (v/v) with contrast media to reach the final rhBMP-2 concentration (0.1 mg/cc) used in the rat ectopic model with ACS. (Reddi A. H., 69 *Proc Natl Acad Sci USA*, 1601 (1972); Urist, M. R., 150 *Science*, 893 (1965); Wozney J. M., et al., 242 *Science*, 1528 (1988)). 7 µl of 4.0 mg/ml rhBMP-2 solution was mixed with 233 µL of Conray®, Omniscan™, or Optiray®. 233 µL of the rhBMP-2 buffer served to dilute the rhBMP-2 control sample.

The implants were set-up in 6-well plates clearly labeled with the implant and animal identification number. A 0.5 cc collagen disc was placed in a single well. 200 µL of 0.1 mg/cc rhBMP-2 in 97% contrast media/3% sterile water was applied to the collagen disc 15 minutes prior to implantation.

Surgical Procedure:

Animals were weighed, anesthetized, and surgically prepared prior to implantation. Preparation for implantation included shaving the abdomen and thorax, and scrubbing these areas with liberal amounts of ChlorohexiDerm™ scrub (DVM Pharmaceuticals, Miami, Fla.). The excess scrub was removed with gauze soaked in ChlorohexiDerm. All animals received four SC implants on the ventral thoracic region in the sterile environment of a surgical suite, and remained under isoflurane anesthesia for the duration of the procedure.

After placing the animal in dorsal recumbency, four incisions (~5 mm in length) were made in each quadrant of the thoracic region (upper right, upper left, lower left, and lower right). The closed tip of the scissors was inserted and spread apart within the SC space. This created a space sufficient to accommodate the implant samples, which were placed with forceps in the SC tissue pocket above the rib cage muscle. Each test implant was placed in each of the four locations listed above in a clockwise rotation. After the implants were placed, the skin around the wound was closed with resorbable suture. All animals were given a SC injection of Nacel (0.8 mg/kg) prior to being placed on their sides in clean, dry cages and observed until they regained their righting reflex.

Animals on study were fed ad libitum and observed daily throughout the study. After 28 days, the animals were sacrificed, and the implants were retrieved by cutting open the skin. The explants were fixed in 10% neutral buffered formalin.

Palpation and Radiography:

Prior to explant, the implants had to be located by manual palpation. Palpation was used to assess the implants according to the scoring system presented in Table 2. Radiographs of the explants were taken to determine bone formation in response to the implants and to localize the site of implantation using high-resolution radiography (Faxitron, Hewlett Packard, McMinnville, Oreg.) and high-resolution film (EK-TASCAN B/RA Film 4153, Kodak, Rochester, N.Y.). Since it is unknown how rapidly these compounds might be cleared from a soft tissue site, histology will also be used to confirm new bone formation, and that data will be compared to the radiographic score. The implant radiographic images were graded according to the coding system presented in Table 3.

TABLE 2

Palpation Coding System

Hard Bone
Soft
Partially Resorbed
Completely Resorbed

TABLE 3

Radiograph Coding System

| 0 = | No bone detected |
| 1+ = | Some bone |
| 2+ = | Moderate bone detected |
| 3+ = | Good bone detected |
| 4+ = | Excellent bone detected |
| 5+ = | Excellent bone detected (larger piece) |

Histology

All samples were labeled and fixed in 10% neutral buffered formalin. After fixation in 10% neutral buffered formalin, decalcification was carried out in 10% disodium ethylenediamine tetra acetate (EDTA) at a pH of 7.5 at 37° C. Periodically, decalcification was monitored radiographically using an X-ray unit. Once the samples were decalcified, the samples were rinsed for 30 minutes in gently running tap water, and processed using a paraffin infiltrator (Shandon-Lipshaw, Chicago, Ill.) to dehydrate the specimens in graded alcohols, clear the specimens with xylene, and infiltrate the tissues with paraffin.

The infiltrated tissue was then embedded in paraffin blocks for sectioning. The blocks were cut on a rotary microtome to produce thin sections between 6 to 8 μm in thickness. Sections were made through the implant site and dermal tissues, and stained with routine H&E, Mallory aniline blue stain, and Toluidine-Blue-O. One author (JT), who was blinded to the treatment groups, used the semi-quantitative scoring system in Table 4 to determine the osteoinductive potential of the implant materials. Aquisition of digital images documenting the osteoinductive potential and host response were made using Image Pro Plus Software (v4.0, Media Cybernetics Inc., Silver Spring, Md.) running on a Windows NT workstation. A video camera (Sony® Hyper HAD CCD-IRIS/RGB, Tokyo, Japan) was used to acquire the digital images through the microscope.

TABLE 4

Histology Semi-quantitative Scoring System

| | |
|---|---|
| 0 = | no bone or marrow |
| 0.5 = | only trace amounts of bone |
| 1 = | bone and marrow, approximately 20% of implant area |
| 2 = | bone and marrow, approximately 40% of implant area |
| 3 = | bone and marrow, approximately 60% of implant area |
| 4 = | bone and marrow, approximately 80% of implant area |
| 5 = | bone and marrow, approximately 100% of implant area |

Results:

The images taken of ACS/Sol-O-Pake® powder demonstrated the need for a liquid medium to thoroughly penetrate the sponge. Even a liberal dusting of the powder on the ACS failed to provide an easy to distinguish image. This result on a tabletop free from the interference of body tissue led Applicants to conclude that a dry powder should not be used for this technique. Directions for use of Sol-O-Pake® include the addition of water to make a liquid medium. In order to avoid the extra step of hydrating a powder for use with INFUSE® Bone Graft, liquid media were chosen for additional testing.

Conray® or Oxilan® 300, two fluid contrast media, was used in this in vitro experiment. Lyophilized rhBMP-2 buffer was reconstituted with 8.4 ml Oxilan® 300. In comparison to WFI, dissolving the powder required an increased amount of agitation due to the viscous nature of this fluid. Aggregates of white powder that were slow to dissolve were seen immediately upon addition of these two contrast media. Upon initial wetting of the ACS sponge with 1.5 ml of this solution, the hydrated sponge had an altered appearance relative to an ACS hydrated with rhBMP-2/buffer as the viscous solution took some time to evenly distribute. After 15 minutes, the flat ACS was translucent. Adding 1.5 ml Conray® to the ACS provided the same initial wetting characteristics that Oxilan 300 demonstrated. After 15 minutes, the Conray® sponge had a stark white appearance when compared to a WFI wetted ACS. ACS hydrated with Conray® or Oxilan 300 provided clear fluoroscopic images of the flat sponge on the bench top.

A 50:50 (v/v) mix of WFI and Oxilan 300 was difficult to mix in a syringe. The application of 1.5 ml of this mixture to the flat ACS provided a similar wetted appearance as a sponge wetted with WFI alone. The fluoroscopic image of the sponge was significantly reduced compared to the ACS containing full strength Oxilan 300. Rolling this sponge according to manufacturer's instructions for insertion of the ACS into an interbody fusion device produced a very dark image.

When Oxilan 300, was serially diluted according to the ratios presented in Table 1, with the wetted ACS sponge placed in the interbody disc space for fluoroscopic imaging, the following results were observed. When the 100% contrast medium wetting ratio (1.4 ml of Oxilan 300 without any rhBMP-2 buffer) was used, the implant was visible under fluoroscopy. When a 57% contrast media wetting ratio (0.8 ml of Oxilan 300 to 0.6 ml of rhBMP-2 buffer) was used, the implant was barely visible under fluoroscopy and its presence was only confirmed upon removal from the disc space. When a 29% or 14% contrast medium wetting ratio was used, the implant was not visible in the interbody disc space. Applicants found that in this region of dense tissue, only those sponges with a high percentage of contrast medium were visible on a fluoroscopic image.

The results from the cadaver study indicated that any attempt to test the efficacy of rhBMP-2 to form bone in the presence of contrast media would require a high percentage of the medium present in the protein solution. Conray®, Omniscan™, and Optiray® were used to dilute a stock rhBMP-2 solution 1:34 (v/v) to make a solution that was 97% contrast media. 200 μl of the resulting solution was applied to a collagen sponge. The three contrast media implants plus one rhBMP-2 alone/collagen implant were surgically placed in a SC pouch on the thoracic region of the rat. Post-operative radiographs were taken verifying the placement of the implants and the efficacy of the technique. After 28 days, the rats were euthanized, and the implants were located and graded by manual palpation (Table 5) for removal. Faxitron images were taken, and based on the amount of potential bone present a grade was assigned (Table 5). The rhBMP-2/ACS implants had a mean score of 4.5 (out of 5). Ominiscan had a mean of 4.0, Optiray had a mean of 2, and the three Conray implants that were identified had a mean of 1.7.

TABLE 5

Examination Results

| ANIMAL | IMPLANT* | PALPATION GRADE | RADIO-GRAPHY GRADE | HISTOL-OGY GRADE |
|---|---|---|---|---|
| 1394 | rhBMP-2 alone | Hard Bone | 4+ | 3 |
| | Conray/rhBMP-2 | Completely Resorbed | N/A | N/A |
| | Omniscan/rhBMP-2 | Hard Bone | 3+ | 4 |
| | Optiray/rhBMP-2 | Hard Bone (Rim Only) | 1+ | 0.5 |
| 1395 | rhBMP-2 alone | Hard Bone | 4+ | 3 |
| | Conray/rhBMP-2 | Hard Bone | 2+ | 3 |
| | Omniscan/rhBMP-2 | Hard Bone | 5+ | 5 |
| | Optiray/rhBMP-2 | Hard Bone (Rim+) | 2+ | 0.5 |
| 1396 | rhBMP-2 alone | Hard Bone | 5+ | 4 |
| | Conray/rhBMP-2 | Hard Bone | 3+ | 2 |
| | Omniscan/rhBMP-2 | Hard Bone | 4+ | 3 |
| | Optiray/rhBMP-2 | Hard | 1+ | 1 |
| 1397 | rhBMP-2 alone | Hard Bone | 5+ | 5 |
| | Conray/rhBMP-2 | Soft | 0 | 0 |
| | Omniscan/rhBMP-2 | Hard Bone | 4+ | 2 |
| | Optiray/rhBMP-2 | Hard Bone | 4+ | 3 |

*All samples contain a 0.1 mg/mL concentration of rhBMP-2.

Finally, the explants were processed for decalcified histology, sectioned, and stained. Scoring of the histology (Table 5) gave a mean bone induction score for the rhBMP-2 sample reconstituted with WFI of 3.8 (range 3-5), indicating that roughly 80% of the cross-sectional area of the implant consisted of bone and marrow decalcified histology micrographs from a subcutaneous implant reconstituted with sterile water for injection. In fact, bone with hematopoietic marrow was observed throughout the implant. The mean bone induction score for the rhBMP-2 sample reconstituted with Omniscan was 3.5 (range 2-5), indicating that roughly 70% of the cross-sectional area of the implant consisted of bone and marrow. This was comparable to the rhBMP-2 control sample, indicating that this particular contrast agent did not interfere with rhBMP-2 induced osteogenesis. The mean bone induction score for the rhBMP-2 samples reconstituted with Conray and Optiray was 1.7 (range 0-3 and one implant totally resorbed) and 1.3 (0.5-3) respectively, indicating that roughly 20% of the cross-sectional area of the implant consisted of bone and marrow. Thus, compared to the control implants, it appears that both Conray® and Optiray® interfered with rhBMP-2 induced osteogenesis in this rat SC model. Comparison of the radiographic score and the histology rating (Table 5) suggest that the response observed on radiographs were new bone formation and not residual contrast agent in the local soft tissue.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

All publications cited in the specification are indicative of the level of skill of those skilled in the art to which this invention pertains. All these publications are herein incorporated by reference to the same extent as if each individual publication were specifically and individually indicated to be incorporated by reference.

The invention claimed is:

1. A bone graft composition comprising (i) an iodine-free contrast media, which comprises gadodiamide, (ii) a bone graft matrix and (iii) an osteoinductive factor comprising BMP-2 at a concentration between about 0.1 mg/ml and about 1.5 mg/ml, wherein the concentration of the gadodiamide is greater than the concentration of the BMP-2 in the bone graft composition and said bone graft composition induces bone formation to about the same extent as a control composition, said control composition comprising the bone graft matrix and the osteoinductive factor but excluding the contrast media, and wherein the osteogenic factor is present in about the same amount in the bone graft composition and the control composition.

2. The bone graft composition of claim 1, wherein said bone graft matrix comprises collagen.

3. The bone graft composition of claim 1, wherein said BMP-2 comprises recombinant human BMP-2.

4. The bone graft composition of claim 1, wherein the gadodiamide and the BMP-2 are in liquid form and the gadodiamide comprises at least 97% by volume based on the total volume of the BMP-2 liquid and gadodiamide liquid in the bone graft composition.

5. The bone graft composition of claim 1, wherein the bone graft composition comprises one part by volume BMP-2 liquid to 34 parts by volume of gadodiamide liquid in the bone graft composition.

6. A bone graft composition comprising: (i) an iodine-free contrast media comprising gadodiamide in liquid form at a concentration of 287 mg/ml; (ii) a bone graft matrix comprising collagen; and (iii) a BMP-2 in liquid form at a concentration between about 0.1 mg/ml and about 1.5 mg/ml, wherein the gadodiamide liquid comprises at least 97% by volume based on the total volume of the BMP-2 liquid and the gadodiamide liquid in the bone graft composition.

7. The bone graft composition of claim 6, wherein the BMP-2 in liquid form is at a concentration of 0.1 mg/ml.

8. The bone graft composition of claim 6, wherein the bone graft composition comprises one part by volume BMP-2 liquid to 34 parts by volume of gadodiamide liquid.

9. A bone graft composition of claim 6, wherein the BMP-2 comprises recombinant human BMP-2.

* * * * *